(12) United States Patent
Wu

(10) Patent No.: US 6,709,617 B2
(45) Date of Patent: Mar. 23, 2004

(54) PROSTHETIC SYSTEM

(75) Inventor: Yeongchi Wu, Darien, IL (US)

(73) Assignee: Physicians Against Land Mines, Chicago, IL (US)

( * ) Notice: Subject to any disclaimer, the term of this patent is extended or adjusted under 35 U.S.C. 154(b) by 262 days.

(21) Appl. No.: 09/921,328

(22) Filed: Aug. 3, 2001

(65) Prior Publication Data

US 2002/0043738 A1 Apr. 18, 2002

Related U.S. Application Data

(60) Provisional application No. 60/222,780, filed on Aug. 3, 2000.

(51) Int. Cl.[7] ............................................. B29C 33/38
(52) U.S. Cl. ........................ 264/222; 264/102; 425/2; 425/175
(58) Field of Search ................. 425/2, 175; 264/222, 264/102, DIG. 30, 313, 227; 623/901

(56) References Cited

U.S. PATENT DOCUMENTS

| | | | |
|---|---|---|---|
| 2,472,754 A | | 6/1949 | Mead |
| 2,473,723 A | * | 6/1949 | Nelson .................... 264/247 |
| 2,488,922 A | | 11/1949 | Mead |
| 2,488,923 A | | 11/1949 | Mead |
| 3,962,395 A | * | 6/1976 | Hagglund .................. 264/222 |
| 5,503,543 A | * | 4/1996 | Laghi ........................... 425/2 |
| 5,578,260 A | * | 11/1996 | De Sena .................... 264/223 |
| 5,971,729 A | * | 10/1999 | Kristinsson et al. ........... 425/2 |
| 5,980,803 A | * | 11/1999 | Stemker et al. ............. 264/222 |

OTHER PUBLICATIONS

Klopsteg et al., "Human Limbs and Their Substitutes," pp. 707–711, McGraw–Hill Book Company, Inc., The Maple Press Company, York, PA (1954).

Wu et al., "An Innovative Removable Rigid Dressing Technique for Below–the–Knee Amputation," *The Journal of Bone and Joint Surgery*, 61–A (5), 724–729 (Jul. 1979).

Wu et al., "Scotchcast® P.V.C. Interim Prosthesis for Below–Knee Amputees," *Bulletin of Prosthetics Research*, 10 (36), 40–45 (1981).

Wu et al., "Removable Rigid Dressing for Below–Knee Amputees," Clinical Prosthetics and Orthotics, 11 (1), 33–44 (1987).

* cited by examiner

*Primary Examiner*—Allan R. Kuhns
(74) *Attorney, Agent, or Firm*—Gardner Carton & Douglas LLP

(57) ABSTRACT

The device and method of the invention utilizes a vacuum pump, a casting device, first and second CIR Connectors, a connector cuff, a casting balloon, a heating chamber or oven, a supracondylar wedge, and a CIR alignment/vacuum forming jig to create a prosthetic device under field conditions.

20 Claims, 16 Drawing Sheets

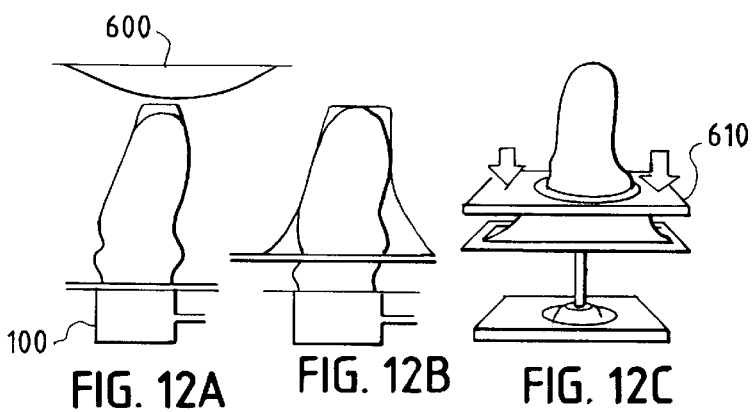
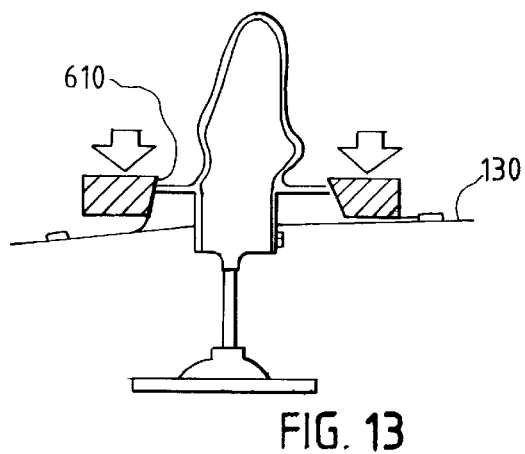
FIG. 12A  FIG. 12B  FIG. 12C
FIG. 13
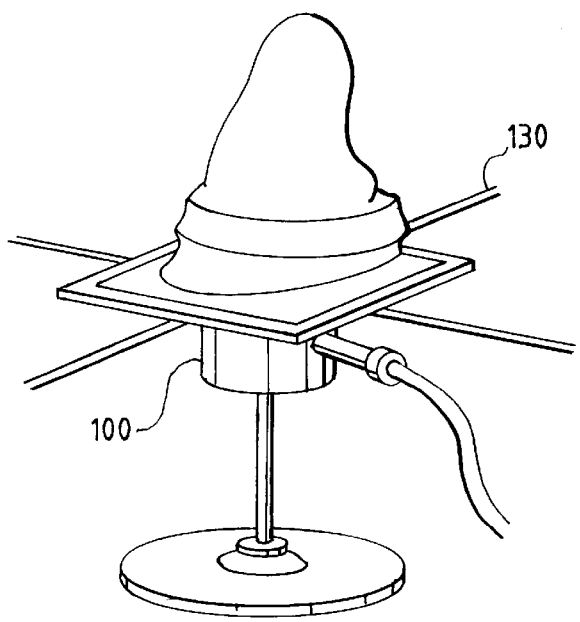
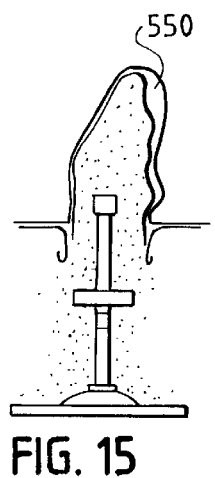
FIG. 14  FIG. 15

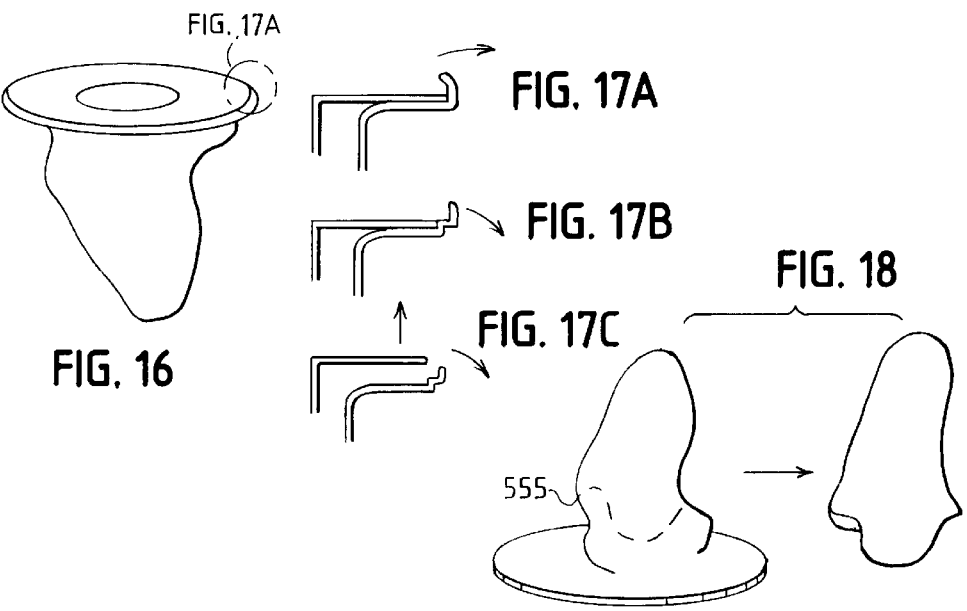
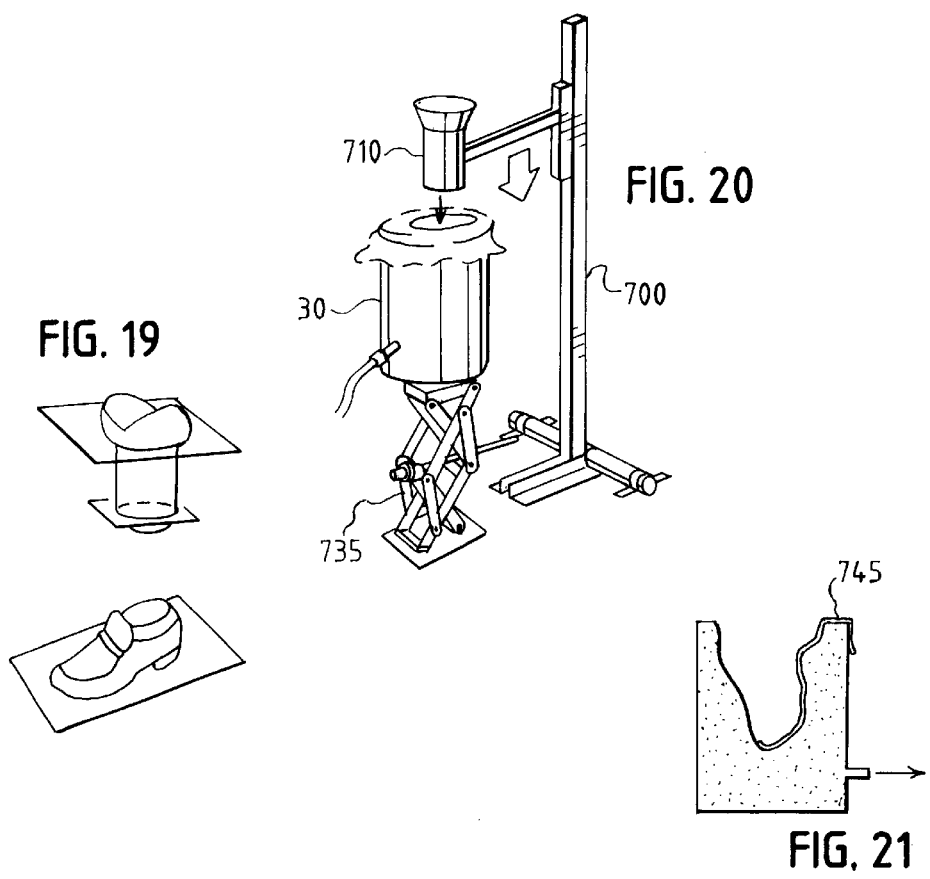

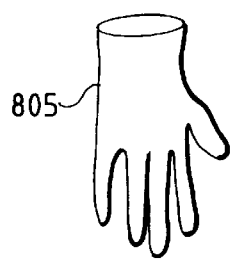
FIG. 36A
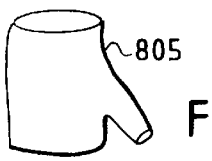
FIG. 36B
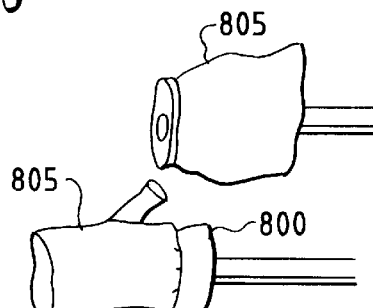
FIG. 36C
FIG. 36D
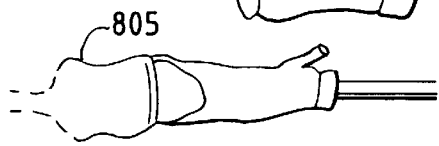
FIG. 36E
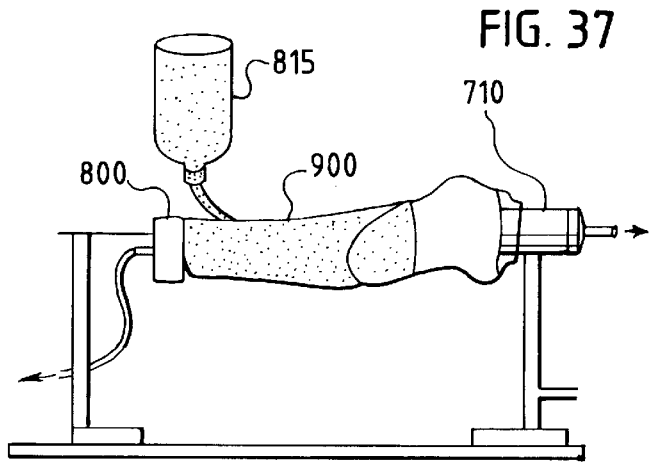
FIG. 37
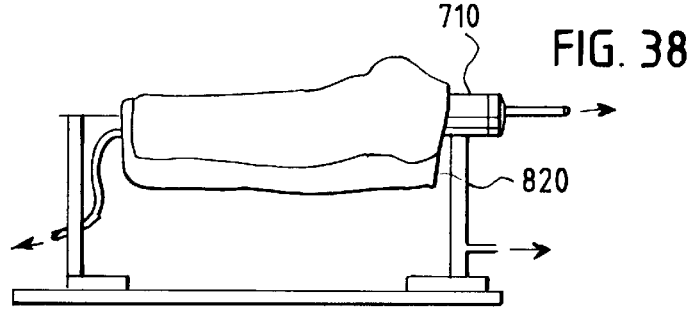
FIG. 38

PROSTHETIC SYSTEM

RELATED APPLICATION

This application claims the benefit of U.S. Provisional Application No. 60/222,780 filed on Aug. 3, 2000.

FIELD OF THE INVENTION

This invention relates to a fabrication procedure using dilatancy devices to make an artificial limb for individuals with transtibial amputation.

BACKGROUND OF INVENTION

Prosthetic limb production is a complicated process. Traditionally, it starts with casting a negative mold of the residual limb using Plaster-of-Paris casting bandages. The negative mold is then filled with Plaster-of-Paris to form a positive model, which is then modified according to the patient's anatomical measurements. Finally, a soft insert is fabricated over the model, followed by lamination with a polyester resin or vacuum forming with a thermoplastic, such as polypropylene, to produce the prosthetic socket. The prosthetic socket is then joined with other components and aligned.

SUMMARY OF INVENTION

In clinical practice, Plaster-of-Paris is still used routinely. The prosthetic system and method of the present invention makes it possible to apply the principle of dilatancy to actually produce transtibial prosthesis or other limb prosthesis as is known in the art without the need for Plaster-of-Paris, which can be difficult to obtain in some situations.

1. Use of recyclable materials, especially the dilatancy casting system, using inexpensive sand to replace Plaster-of-Paris for forming a negative mold and positive model.

2. Use low-cost, portable equipment for alignment and forming of transtibial prosthesis. The equipment can be easily transported and maintained, to reduce initial set up and maintenance cost.

3. Use a simplified alignment approach, which was previously developed for Scotchcast prosthesis, to improve accuracy and minimize technical errors. Our laboratory trial showed that the procedure could provide rapid formation of a negative mold of a patient's residual limb. The negative mold can be converted into a positive replica of the residual limb. From this positive model, a prosthetic socket can be made.

BRIEF DESCRIPTION OF THE DRAWINGS

FIGS. 12a–12c illustrate side elevation and perspective views of the positive model of FIG. 11 in embodiments of the steps of preparing a polypropylene socket by vacuum forming in a method of the present invention.

FIG. 13 illustrates a side elevation, sectional view of the positive model of FIG. 11 in an embodiment of a step of preparing a polypropylene socket by vacuum forming following the steps of FIG. 12 in a method of the present invention.

FIG. 14 illustrates a perspective view of the positive model of FIG. 11 in an embodiment of a step of preparing a polypropylene socket by vacuum forming following the step of FIG. 13 in a method of the present invention.

FIG. 15 illustrates a side elevation, sectional view of the positive model of FIG. 11 in an embodiment of a step of preparing a polypropylene socket by vacuum forming following the step of FIG. 14 in a method of the present invention.

FIG. 16 illustrates a perspective view of the polypropylene socket of FIGS. 12–15 in an embodiment of a step of preparing a polypropylene socket by vacuum forming following the step of FIG. 15 in a method of the present invention.

FIGS. 17a–17c illustrate fragmentary, sectional views along the circular arc of FIG. 16 of the steps for removal of the polypropylene socket of FIGS. 12–16 from the flange of the connector of FIG. 9 in an embodiment of a step of preparing a polypropylene socket by vacuum forming following the step of FIG. 16 in a method of the present invention.

FIG. 18 illustrates a perspective view of the polypropylene socket of FIGS. 12–16 in an embodiment of a step of preparing a polypropylene socket by vacuum forming following the step of FIG. 17 in a method of the present invention.

FIG. 19 illustrates a perspective view of a socket and a foot in an embodiment of a step for determining an alignment axis in preparing an exoskeletal prosthesis in a method of the present invention.

FIG. 20 illustrates a perspective view of an alignment vacuum forming jig positioned over a negative mold in a dilatancy device supported by a jack including a plumb line which represents the alignment axis in embodiments in an alternative embodiment of a step for determining an alignment axis and a height of a socket axis in preparing an exoskeletal prosthesis in a method of the present invention.

FIG. 21 illustrates a side elevation, sectional view of a negative mold in an embodiment of a step in preparing an exoskeletal prosthesis following the step of FIG. 20 in a method of the present invention.

FIGS. 36a–36e illustrate a fragmentary, perspective view of a latex glove having a first opening and having the fingers cut out to form a second opening, the second opening further connected to the ankle block including the position attachment of FIG. 35, the first opening further connected to the polypropylene socket of FIG. 29, the latex glove further having the thumb tip cut open, in embodiments of the steps of preparing an exoskeletal prosthesis following the step of FIG. 35 in a method of the present invention.

FIG. 37 illustrates a side elevation view of the horizontally tilted alignment vacuum forming jig having the polypropylene socket of FIG. 29, or the horizontally tilted alignment vacuum forming jig having the positive model of FIG. 28, the horizontally tilted alignment vacuum forming jig further including the ankle block including the position attachment of FIG. 35, the polypropylene socket and the ankle block further connected by the latex glove of FIG. 36, in an embodiment of a step of preparing a positive model of a shank in preparing an exoskeletal prosthesis following the step of FIG. 36 in a method of the present invention.

FIG. 38 illustrates a side elevation view of the horizontally tilted alignment vacuum forming jig having the positive model of a shank of FIG. 37 in an embodiment of a step of preparing a polypropylene shank by vacuum forming in preparing an exoskeletal prosthesis following the step of FIG. 37 in a method of the present invention.

DETAILED DESCRIPTION

The dilatancy systems and methods of the present invention are hereinafter referred to as the CIR (Center for International Rehabilitation) dilatancy systems and methods. The following serve to illustrate embodiments of the present invention.

The dilatancy system for prosthesis fabrication is designed to be inexpensive for initial set up and portable for service delivery. The equipment includes a vacuum pump, a dilatancy-casting device, CIR Dilatancy Connectors #1 and #2, a latex connector cuff, a large latex casting balloon, a heating chamber or oven, an adjustable stand, a supracondylar wedge, and a CIR alignment/vacuum forming jig. Each item is described below:

1. Vacuum Pump

Any type of vacuum pump used in most prosthetic workshops will serve adequately. Negative pressure of 10-20 psi (pound per square inch) is sufficient, although higher pressures may be used. In our development process, a USMC (U.S. Manufacture Company) vacuum-forming system was used (not shown). The system consists of a vacuum pump with a ⅛ HP motor and an 8-gallon accumulator tank that permits easy control of the vacuum by a foot-actuated control valve. The system is capable of producing about 26 psi.

2. CIR Dilatancy Casting Device

The dilatancy casting device consists of a plastic or metal container filled with fine sand granules. It has an air hose connector on one side to be connected to a vacuum pump. The inner opening of the air hose connector is covered with layers of a flexible semi-permeable substance, such as a cloth, that acts as a filter to prevent the sand from being sucked into the vacuum pump. The container is placed on a platform, which has an extra space for the patient to stand. Blocks of plywood or an automobile jack can be used to raise the height of casting device according to patient's height. The dilatancy-casting device can also be made from a fluidized sand container.

3. CIR Dilatancy Connectors #1 and #2

Figure 1:
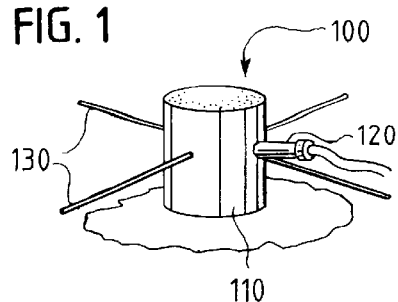
FIG. 1 illustrates a perspective view of one embodiment of a dilatancy connector of the present invention.
Figure 2:
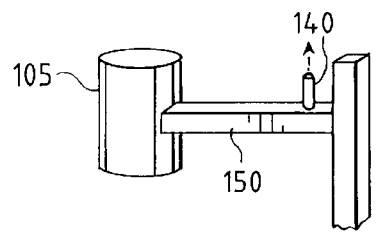
FIG. 2 illustrates a fragmentary, perspective view of an alternative embodiment of a dilatancy connector of the present invention.
Figure 5:
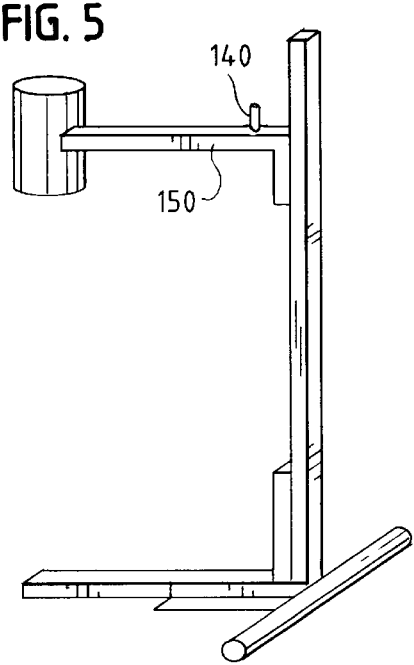
FIG. 5 illustrates a perspective view of one embodiment of an alignment vacuum forming jig of the present invention.

In one embodiment, the CIR Dilatancy Connector #1 100 as is shown in FIG. 1 in this embodiment, is a stainless metal tube 110, 3-inch inside diameter, with a flange, 6 inch outside diameter. On one side of the metal tube, an air hose connector 120 was welded. A layer of fabric is glued onto the inside surface of the metal tube continuing onto one side of the flange. Four metal bars 130 attached to the side of the CIR Dilatancy Connector #1 will be used to hold the heated steel frame and plastic during vacuum forming of the prosthetic socket. A latex cuff is used to seal the space between the CIR Dilatancy Connector #1 and the dilatancy-casting device. As shown in FIGS. 2 and 5, CIR Connector #2 is a different design, which has a larger pipe 105, 2 inches in diameter welded to one end of the mandrel 150. There is an air outlet from the side of the wider pipe 140 and another air outlet from one end of the mandrel 150. The other end of the mandrel 150 also has a filter attached.

4. Casting Balloon

Figure 3:
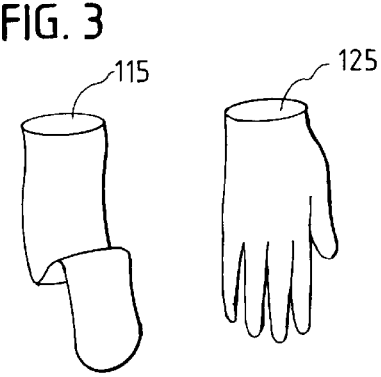
FIG. 3 illustrates a perspective view of a latex casting balloon and a latex glove used in one embodiment of the present invention.

A large casting balloon 115 is used to convert the negative mold of a dilatancy casting device into a positive replica of the residual limb. The positive model is covered by a latex casting balloon used for vacuum forming the prosthetic socket. A large surgical latex glove 125 can also be used for dilatancy casting as can be seen in FIG. 3.

5. Heating Chamber or Oven

A commercial pizza oven works well, yet, for portability and low set up cost, a heating element in a sandwich arrangement inside an insulated package works conveniently. A flexible heating package may also be used.

6. Automobile Jack

Figure 4:
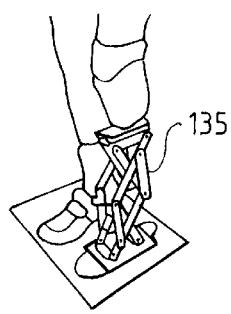
FIG. 4 illustrates a perspective view of an adjustable stand used in one embodiment of the present invention.

A simple adjustable stand can be made of ordinary automobile scissors jack. The jack 135 is attached to a 2×2-foot plywood as is shown in FIG. 4. Its top plate is padded and covered with durable leather lining. This inexpensive automobile jack can be used for prosthetic alignment.

7. Supracondylar Wedge

Varying sizes and shapes of a flexible wedge are used for build up of the supracondylar pouch. This is done on some patients to avoid problems of undercut during fabrication of negative molds. The wedge can be made of polyurethane or aluminum foil.

8. CIR Alignment/Vacuum Forming Jig (CIR-AVF jig)

The CIR alignment vacuum forming Jig is a specially designed fixture as is shown in FIG. 5 used for making a MonoLimb. This specially designed fixture allows prosthesis alignment in a vertical position and vacuum drape forming of the socket in a horizontal position when used for making a CIR MonoLimb. For example, for a transtibial endoskeletal prosthesis, the device for alignment can be done with a simple plumb line going through a fixed point. It should be understood that the CIR alignment jig may include a dilatancy device that may further include an attachment to allow the positioning of the ankle block in various directional alignments.

9. Mandrel and Base Plate

Figure 6:
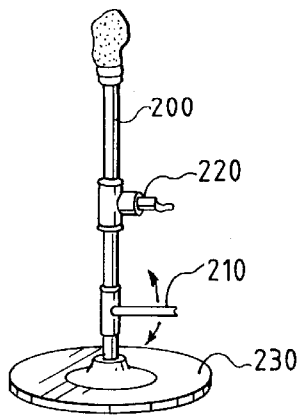
FIG. 6 illustrates a perspective view of one embodiment of a mandrel of the present invention.

Alternatively, a mandrel may be made of a steel pipe 200 with an air valve 210 close to one end and a filter on the other end. In between, there is an air outlet 220 to be connected to a vacuum pump as is shown in FIG. 6. The end without the filter may be attached to a base plate 230.

EXAMPLE 1

Transtibial Polypropylene Socket

The process of making a CIR socket includes: a) preparing the residual limb, b) creating the negative mold, c) forming the positive model, and d) vacuum forming the polypropylene socket. The residual limb to be cast should be shrunk and not bulbous in shape. The process for forming a socket as described herein provides a total contact socket. However, pressure bearing in the socket can be modified to either increase or decrease final pressure bearing at several stages of the casting process.

Figures 7A, 7B, 7C:
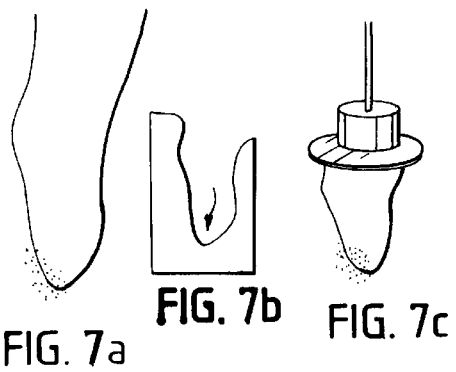
FIG. 7a illustrates a fragmentary, perspective view of a residual limb in one embodiment of a step to reduce pressure bearing in a socket made by a method of the present invention.
FIG. 7b illustrates a side elevation, sectional view of a negative mold in an alternative embodiment of a step to reduce pressure bearing in a socket made by a method of the present invention.
FIG. 7c illustrates a fragmentary, perspective view of a positive model in an alternative embodiment of a step to reduce pressure bering in a socket made by a method of the present invention.

There are many ways to reduce pressure bearing. These may include:

1. Build-up with cotton padding on the residual limb before the negative mold is created as shown in FIG. 7a;

2. Making indentations inside the negative mold before the positive model is made as shown in FIG. 7b, and/or 3. Adding clay build-up after the positive model is obtained but before the socket is formed as is illustrated in FIG. 7c.

Figures 8A, 8B:
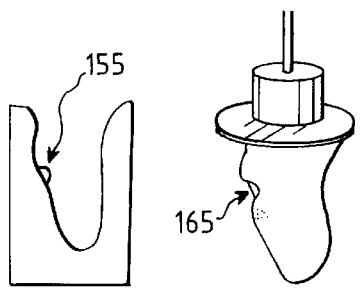
FIG. 8a illustrates a side elevation, sectional view of a negative mold in one embodiment of a step to increase pressure bearing in a socket made by a method of the present invention.
FIG. 8b illustrates a fragmentary, perspective view of a positive model in an alternative embodiment of a step to increase pressure bearing in a socket made by a method of the present invention.

For increased pressure bearing, building up clay 155 on the negative mold or making an indentation 165 on the positive model may also be used as is further illustrated in FIG. 8.

A. Preparing the Residual Limb

1. On the residual limb 10, apply a prosthetic sock 300 or sport tube sock, which keeps cotton padding (for pressure relief) from being displaced.

Figure 9A:
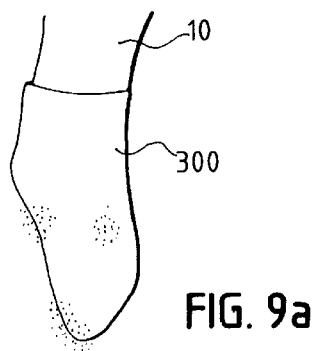
FIGS. 9a–9k illustrate fragmentary, perspective views of a residual limb in embodiments of the steps of preparing a residual limb and creating a negative mold in a method of the present invention.

2. Apply padding such as, for example, cotton padding, over the tibial crest, tibial tubercle, end of tibial bone and the fibular head for pressure relief. The number of layers of padding is determined by the degree of underlying bony prominence, i.e. the more padding is used wherever the more relief is required as is shown in FIG. 9a.

Figure 9B:
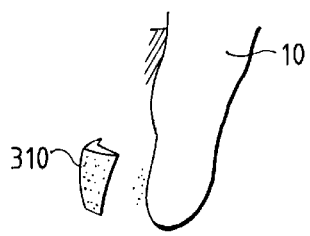

3. Place layers of padding (or a pre-made wedge 310) onto the medial supracondylar area to increase the width so that a wider opening of the negative mold can be made. This will avoid an under cut and allow the residual limb to be removed without significant difficulty later as shown in FIG. 9b. The flexible wedges in various sizes and shapes can be made with, for example, foams such as polyurethane, aluminum foil, or many other malleable substances suitable for such purposes.

Figure 9C:
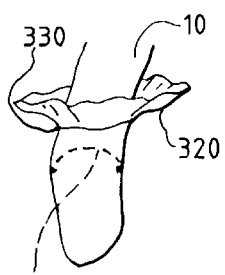

4. Cover the padded residual limb with a thin airtight sheet such as but not limited to a plastic bag or a sheet of rubber 320, which is then held to the residual limb 10 by application of a rubber band 330. Then, mark the trim line 335, for example in a transtibial prosthesis, the patellar tendon area and mediollateral trim line, posterior wall and the hamstrings using, for instance, black electrical tape as shown in FIG. 9c.

Figure 9D:
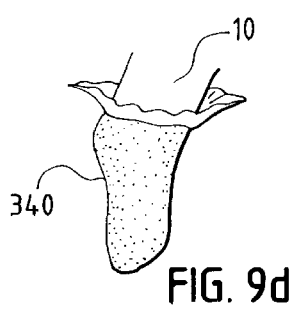

5. Apply a fitted covering 340 over the airtight sheet and residual limb 10 such as but not limited to a short 5-ply wool sock, to assure the airtight sheet contacts the skin for a smooth surface of the negative mold as is illustrated in FIG. 9d.

Figure 9E:
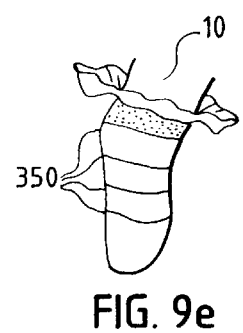

6. Apply about 2 layers of a removable pressurized coating such as but not limited to an elastic stockinette 350 with various lengths as seen in FIG. 9e, therein providing a gradient pressure from distal to proximal. Distal end of the coating is sewn before application.

7. Alternatively, a latex sleeve may be provided. The latex sleeve covers the limb such that the sleeve can then be pulled over the dilatancy casting container to form a seal over the container.

B. Creating the Negative Mold

Figure 9F:
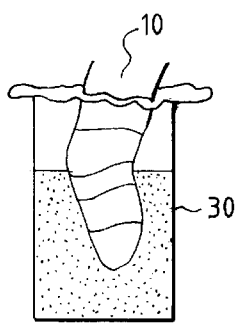

1. While the patient is in an upright position, position the residual limb 10 in the center of the dilatancy casting container 30 and fill the container 30 with sand to the appropriate level, for instance, with a transtibial amputation, to the patellar tendon level as is shown in FIG. 9f.

Figure 9G:
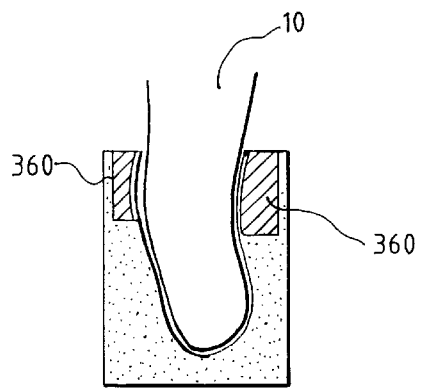
Figure 9H:
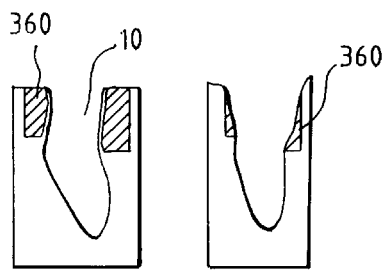

2. Place a soft sponge 360 in places where flaring is desired and to minimize undercut, for instance with the transtibial residual limb 10, place a soft sponge 360, about the width of the knee and 3 or 4 inches high in the back so that the lower margin of the sponge 360 is leveled with the patellar tendon. Place another piece of sponge 360, about the width of the patella and 3 to 4 inches high, right above the patella. Then fill the container with sand to the brim. Tap the container 30 and pack the sand such that the negative mold will be in total contact with the residual limb 10 as is illustrated by FIG. 9g. The purpose of placing 2 sponges in the front and back of the knee is to create space for a flared posterior trim line and for avoiding undercut in and above the patella as is shown in FIG. 9h.

Figure 9I:
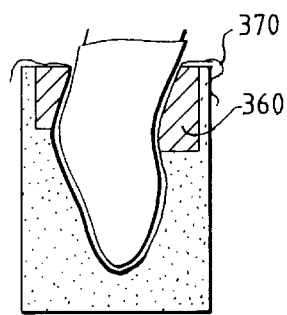

3. Bring the airtight sheet or, alternatively the latex sleeve covering the limb, over the brim to seal sand in the container. One type of a sealing means includes, but is not limited to a rubber band 370 as is shown in FIG. 9i. The set up with the residual limb 10 in place is further shown in FIG. 9i.

Figure 9J:
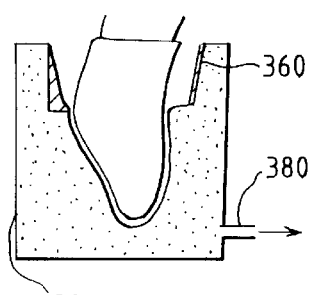

4. Connect air hose #1 380 to the sand container 30 and turn on the vacuum such that the air is removed from the container 30. Within a few seconds the sand in the dilatancy device will become a solid negative mold of the residual limb as is illustrated in FIG. 9j. The soft sponges 360 will collapse under the negative pressure to create enough space in the front for limb withdrawal and adequate space in the back for forming a nice posterior trim line.

Figure 9K:
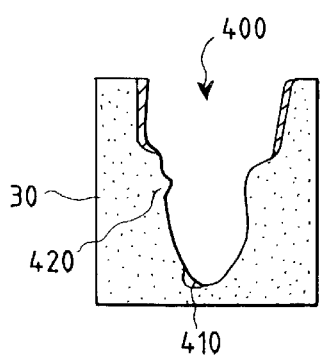

5. After the residual limb 10 is withdrawn from the negative mold 400, modification can be done at this time on the negative mold 400. For intended pressure relief, apply pressure on the surface of the negative mold for making indentations 410. For increase pressure bearing of a final socket, add clay build-up 420 on the surface of the negative mold 400. This can also be done by making an indentation on the positive model at a later point in time and is illustrated by FIG. 9k.

C. Making the Positive Model

Figure 9L:
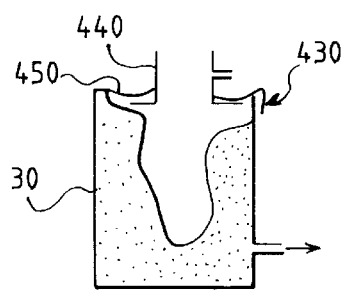
FIGS. 9l–9n illustrate side elevation, sectional views of the negative mold of FIGS. 9a–9k including a connector having a flange in embodiments of the steps of preparing a positive model in a method of the present invention.

1. Upon satisfaction of the completed shape of the negative mold, apply a strip of sheath, such as but not limited to a nylon sheath 430 from the bottom of the negative mold to the brim of the sand container Tape one end of the nylon sheath 430 with a strip of black electric tape to the bottom of the negative mold. This black tape serves as a landmark to make sure that the casting balloon used in the next step is fully in contact with the negative mold. The strip of nylon sheath is to assure removal of air between the casting balloon and the negative mold. Then, bring CIR Connector #1 440 and seal the lower part of the CIR Connector #1 440 to the sand container 30 with another latex cuff 450 as is illustrated in FIG. 9L.

Figure 9M:
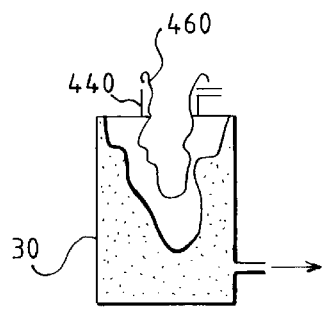

2. Place a large latex casting balloon 460 into the CIR Connector #1 440 and seal the connector with the same balloon as is shown in FIG. 9m.

Figure 9N:
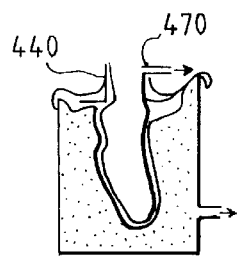

3. Connect a second air hose 470 from the vacuum pump to the side of the CIR Connector #1 440 as is shown in FIG. 9n and remove the air from the space between the casting balloon 460 and the negative mold 400.

Figure 10:
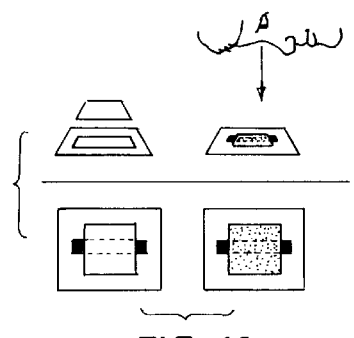
FIG. 10 illustrates a schematic and a plan view of a visible inspection of a strip of black tape as seen through a casting balloon within the negative mold of FIG. 9 in an embodiment of a step in preparing a positive model following the steps of FIG. 9 in a method of the present invention.

4. Watch the casting balloon 460 as it expands into the negative mold. Once the black electric tape in the bottom of the negative mold appears through the casting balloon, the casting balloon is generally in total contact with the negative mold as can be seen in FIG. 10.

Figure 11A:
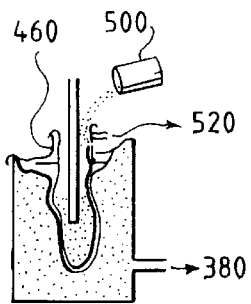
FIGS. 11a–11g illustrate side elevation, sectional views of the negative mold of FIG. 9 and a positive model in embodiments of the steps of preparing a positive model following the steps of FIGS. 9 and 10 in a method of the present invention.
Figure 11D:
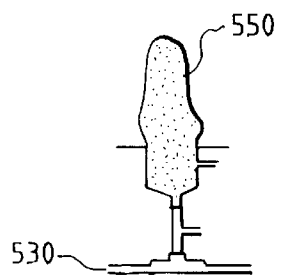
Figure 11B:
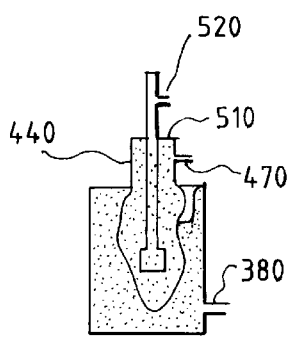

5. Insert a mandrel 500 into the casting balloon 460 and then fill the space with sand to its brim. Seal the top end of the CIR Connector #1 440 with another latex covering 510 such as a balloon as is illustrated in FIGS. 11a and 11b.

6. Connect an air hose 520 to the vacuum pump and remove the air to solidify the sand in the casting balloon 460 to form a positive model as is shown in FIG. 11b.

Figure 11E:
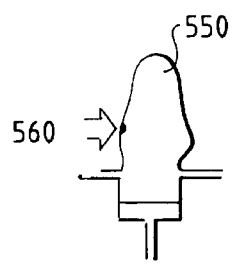
Figure 11C:
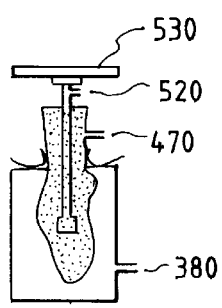

7. Once the positive model becomes solid under negative pressure, disconnect the air hose 470 from the CIR Connector #1 440 and the air hose 380 from the dilatancy device. This allows the negative mold to become a loose mass of sand as can be seen in FIG. 11c.

8. Attach the base plate 530 to the mandrel, then remove the solid positive model 550 from the loosened sand mass in the sand container. Place the positive model upside down on its base plate on a working table as is illustrated in FIG. 11d. At this time, the positive model 550 is ready for further modification as needed before vacuum forming of the polypropylene socket.

Figure 11F:
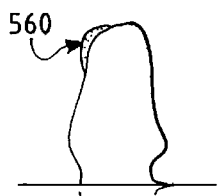

9. At this time, the positive model 550 can still be modified for pressure relief or pressure bearing in the final socket. Pushing the sand to make indentations 560 will increase pressure bearing in the formed socket as is shown in FIG. 11e. For additional pressure relief in the socket, one can make build up of the positive model with, for instance, water based clay 560 before vacuum forming the socket as is illustrated in FIG. 11f.

Figure 11G:
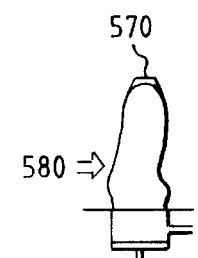

At this time, various steps may be taken, depending on the type of socket planned. For example, in an endoskeletal prosthesis with surpacondylar suspension, add an end pad 570, a ½ inch pelite 580, and a pyramid coupling plate as shown in FIG. 11g. Position them properly so that it is in alignment with the pylon to be attached later.

For suction socket with silicon sleeve and pin shutter set up, a silicon sleeve may be applied before the negative mold is made. The pin-shutter unit is then applied later over the positive model.

For exoskeletal prosthesis, the socket can be formed with or without an end pad or the pyramid connector couplings. Detailed steps for drape forming a socket for CIR exoskeletal prosthesis will be discussed in another section.

D. Alternate Method for Making a Negative Mold and a Positive Model

In a preferred embodiment as illustrated in FIGS. 41–51 of the present invention for making a socket for a prosthesis, there is provided a container 30 adapted to hold a residual, such as, but not limited to a residual limb that may remain after amputation of a leg or other limb. The residual limb 10 is first covered with a plastic bag (not shown) and then subsequently covered with a pliable sheet 20 such as rubber or latex. After covering the residual limb 10, the residual limb 10 is centrally placed within the container 30 which may be a metal or plastic container as has been described herein.

Figure 42:
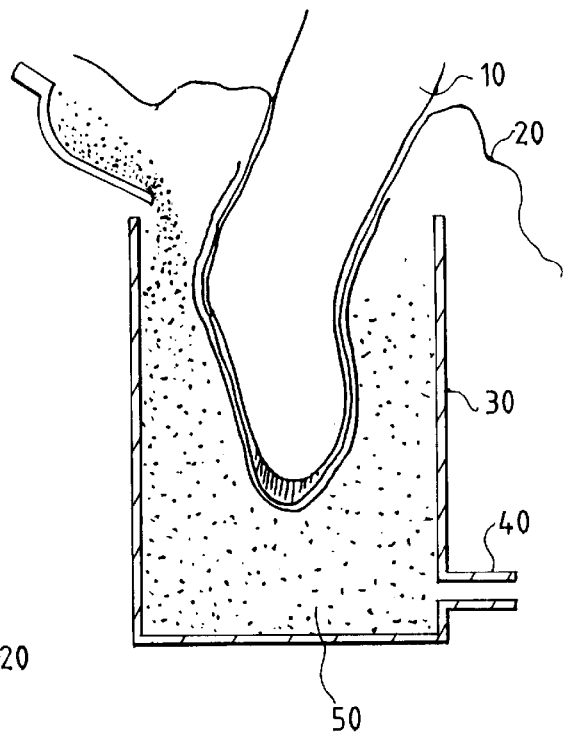
Figure 43:
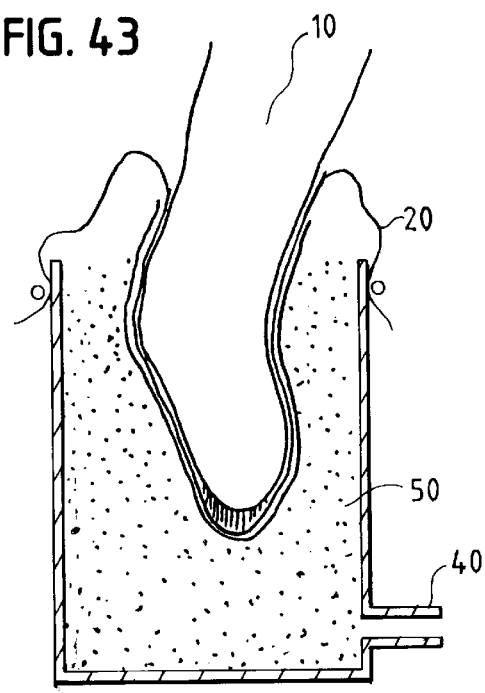
Figure 44:
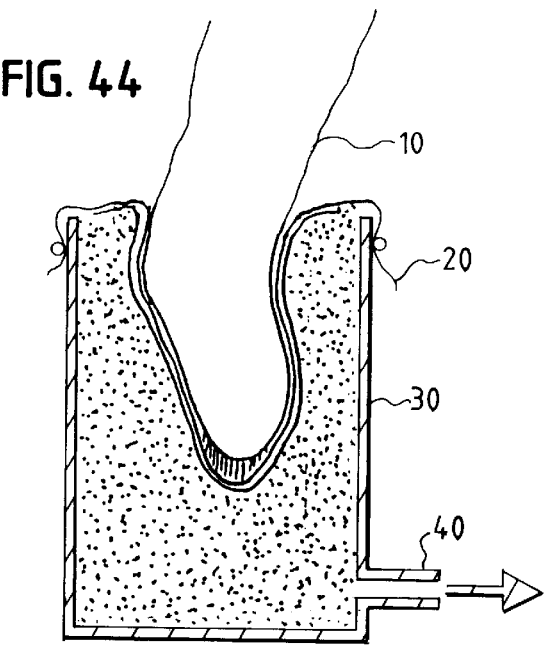
Figure 45:
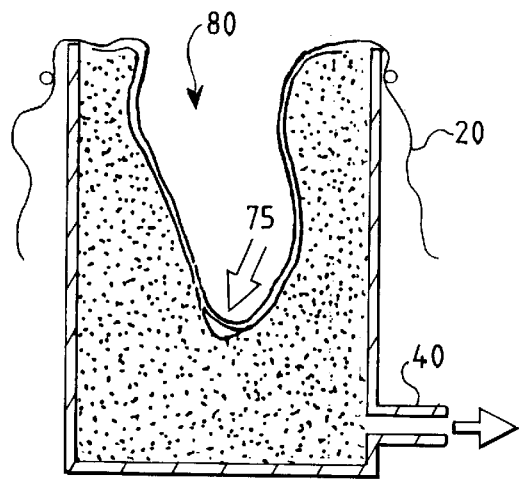
Figure 46:
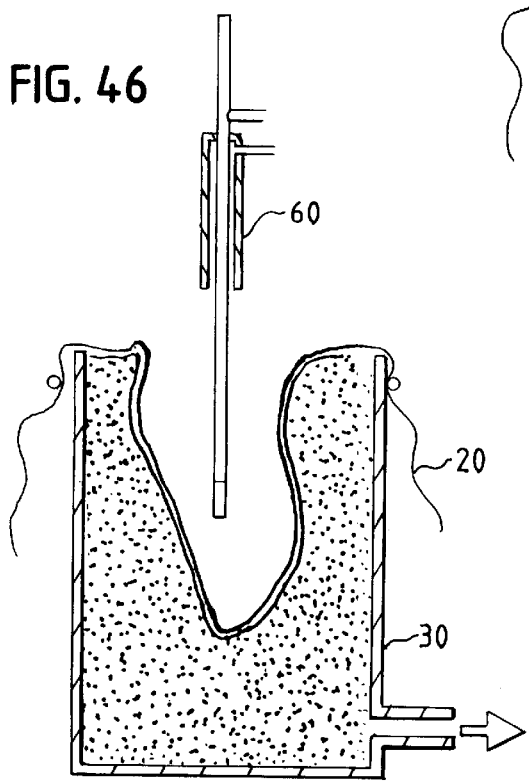
Figure 47:
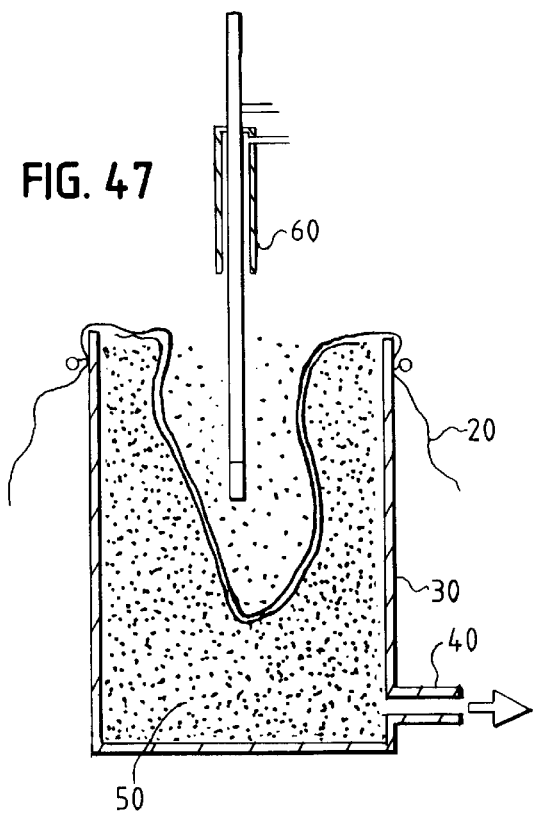
Figure 48:
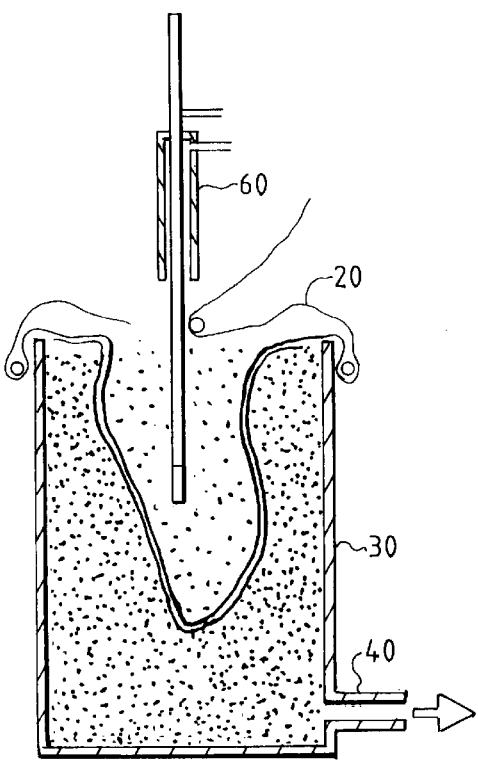
Figure 49:
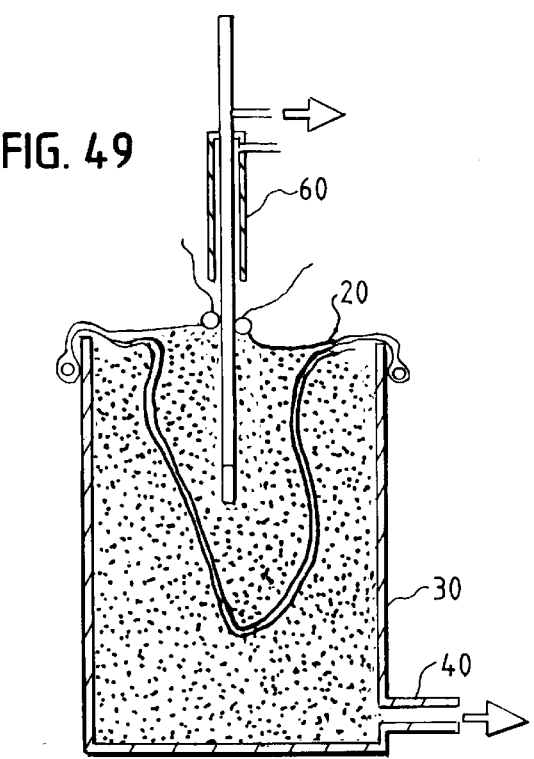

After the residual limb 10 has been prepared as described herein and placed in the container 30, sand is poured around the limb such that the container is filled to the brim as is illustrated in FIG. 42. After filling the container 30 with sand, the pliable sheet 20 covering the residual limb 10 is stretched to cover the container 30, thus forming a seal over the top of the container 30 as shown in FIG. 43. A vacuum source (not shown) having an air hose 40 is then attached to the container 30 such that the air can be removed from the sand. A filter is secured between the air hose 40 and the container 30 for preventing the sand from being removed from the container 30. Once the vacuum source is turned on and the air is removed, the sand solidifies to form a negative mold 80 of the residual limb. The negative mold 80 can then be formed or further molded or adjusted to provide pressure relief by adding clay or any other substance for forming the negative mold 80 into a more preferred shape.

Figure 50:
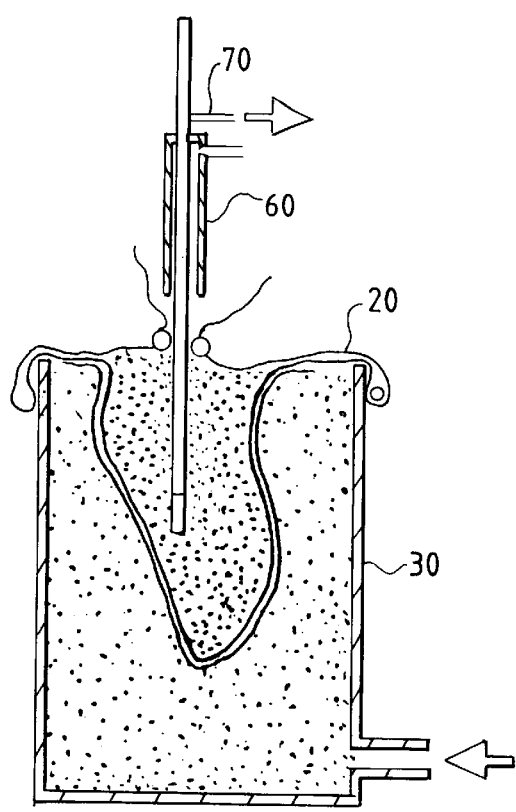
Figure 51:
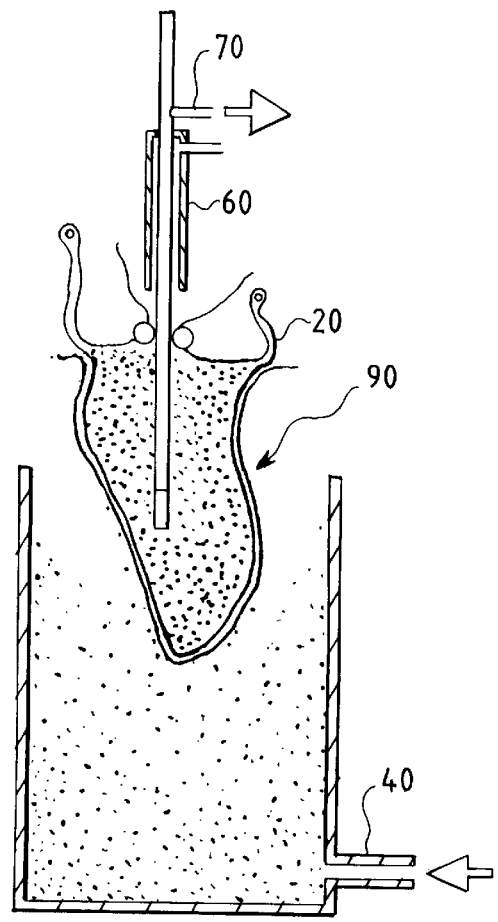

Upon creating the negative mold 80, the CIR Connector #2 60 is positioned within the negative mold 80 such that sand is poured around the mold. Once the negative mold 80 is filled with sand and the CIR Connector #2 60 is secured, the pliable sheet 20 is stretched and further attached to the CIR Connector #2 60, thus forming a seal over the negative mold 80. A second vacuum source (not shown) is attached to the CIR Connector #2 60 via an air hose 70 and a filter, the second vacuum source removing the air from the sand contained within the negative mold 80. The sand then solidifies to form a positive model 90 of the residual limb. The first vacuum source is removed or turned off such that the negative mold 80 becomes fluidized as is shown in FIGS. 50–51 and the positive model 90 can then be removed from the container 30.

D. Vacuum Forming Polypropylene Socket

The process of vacuum forming a polypropylene socket is similar to that used in routine socket fabrication.

1. First, attach 4 threaded rods 130 into the long nuts on the side of the CIR Connector #1 100. The metal rods 130 will support a heated metal frame that holds polypropylene during vacuum forming of the socket.

2. Apply a nylon stocking over the positive model, as routinely used for vacuum forming of a plastic socket, and connect an air hose to the side of the CIR Connector #1 100.

3. Bring the heated and softened polypropylene to bubble 600 forming the socket as is shown in FIGS. 12a–c. Use a metal ring 610 or a nylon rope to make sure there is a complete seal of the softened polypropylene along the flange of the CIR Connector #1 100 as shown in FIG. 13. Apply vacuum and make sure the plastic is formed properly on the positive model.

4. The hot frame that holds the polypropylene can rest on the threaded rods 130 attached to the CIR Connector #1 100 while the excessive plastic is being cut off as illustrated in FIG. 14.

5. Wait until the plastic socket is cooled and becomes rigid, disconnect both the air hose to the mandrel and the air hose to the CIR Connector #1 100 to allow air to enter the space between positive model 550 and the formed socket. Then open the latex cover on the top of the positive model to drain the sand out of the balloon. Remove the mandrel and proceed to cut the newly formed socket out of the CIR Connector #1 100 as is illustrated in FIG. 15.

6. While the plastic is still hot and soft, cut as close as possible along the flange of the CIR Connector #1 100 as is shown in FIG. 16. Then use a pointed cutter to cut the overhung plastic at 1 or 2 inch intervals. Once the plastic is cooled, bend the overhung plastic and remove the socket as illustrated in FIGS. 17a–c.

7. Outline the trim line 555 with a china marker and cut along the marked line using a plaster cutter as is illustrated in FIG. 18. After buffering the trim line, the socket is ready for assembling with a pylon and foot-shoe unit.

Transtibial Exoskeletal Prosthesis

The process for creating transtibial exoskeletal prosthesis is a quite different approach. The dilatancy casting system is not only used for making the prosthetic socket, but also the shank that join the socket to the prosthetic foot. The process of joining the socket and the shank is done on a specially designed alignment jig, which also is used to drape vacuum forming the shank onto the socket.

The steps for a detailed process according to one embodiment of the present invention include:

1. Making a negative mold of the residual limb using a dilatancy casting system, which is described in the section of "making a negative mold for a polypropylene socket."

2. Convert the negative mold into a positive model using the CIR Alignment/Vacuum forming jig.

3. Drape forming a prosthetic socket on the CIR Alignment-vacuum forming jig (CIR AVF Jig)

4. Making a dilatancy mold for a prosthetic shank.

5. Drape forming the prosthetic shank onto the prosthetic socket.

A. Making the Negative Mold of a Residual Limb

The steps are identical to that described above for making a negative mold. Before the patient withdraws his limb from the dilatancy device, the patient can bear weight on the amputated limb to test the comfort in the negative mold.

Determining "Axis" and "Height" of the Socket

1. While checking for a comfortable fit, also adjust the position of the negative mold such that the height and axis of the negative mold can be duplicated in the exoskeletal socket While standing, adjust the automobile jack 735 until the pelvis is even on both sides. The position of the negative mold represents the position of the prosthetic socket to be made.

2. Move the negative mold (the dilatancy device) on to a working table where the CIR AVF jig 700 is attached as is shown in FIGS. 19–20. Drop a plumb line, which represents the alignment axis, through a fixed point on the CIR AVF jig 700 down into the negative mold. The plumb line should point at the socket center, which is the geometric center at the cross-section at the level of the patellar tendon. A strip of nylon sheath 745 should be taped to the bottom of the negative mold and extend to the brim as seen in FIG. 21.

B. Making a Positive Model

Figures 22, 23:
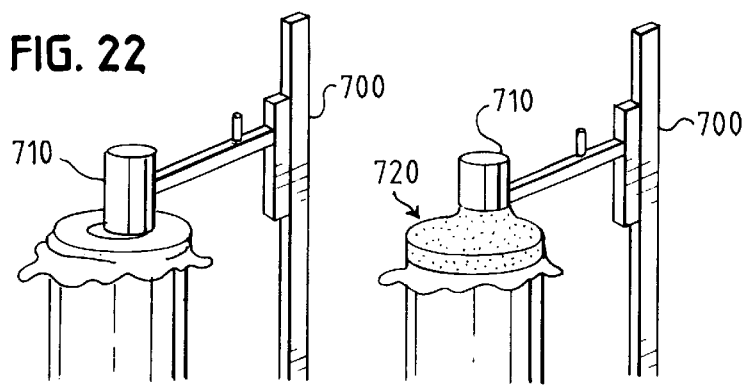
FIG. 22 illustrates a fragmentary, perspective view of the alignment vacuum forming jig and the negative mold of FIG. 20 in an embodiment of a step in preparing an exoskeletal prosthesis following the step of FIG. 21 in a method of the present invention.
FIG. 23 illustrates a fragmentary, perspective view of the alignment vacuum forming jig and the negative mold of FIG. 20 in an embodiment of a step in preparing an exoskeletal prosthesis following the step of FIG. 22 in a method of the present invention.

1. Place the CIR Connector #2 710 into the negative mold and fill the negative mold with sand to its brim and seal the dilatancy device with a latex cuff 720 as is illustrated in FIGS. 22–23. The center of the CIR Connector #2 710 should match the alignment axis as represented by the plumb line.

2. Cover the top with the same plastic sheath to the CIR Connector #2 710 and connect the air outlet on one end of the CIR Connector #2 to a vacuum pump. Once the vacuum pump is turned on the sand will become a solid positive model as was described herein.

Figure 24:
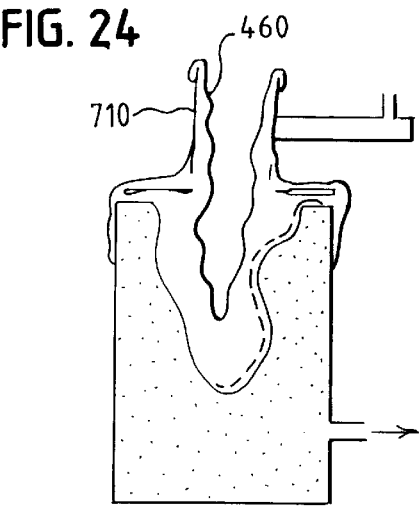
FIGS. 24–26 illustrate side elevation, sectional views of the alignment vacuum forming jig and the negative mold of FIG. 20 in embodiments of the steps of preparing a positive model in preparing an exoskeletal prosthesis following the step of FIG. 23 in a method of the present invention.
Figure 25:
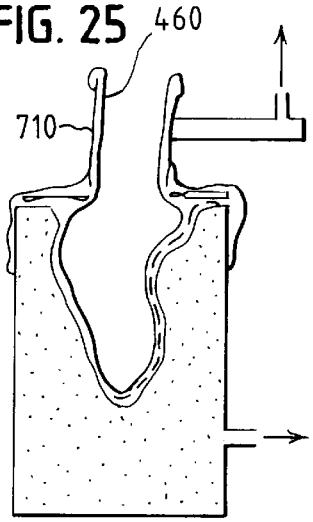
Figure 26:
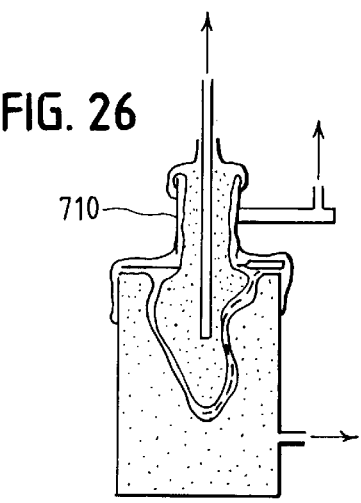
Figure 27:
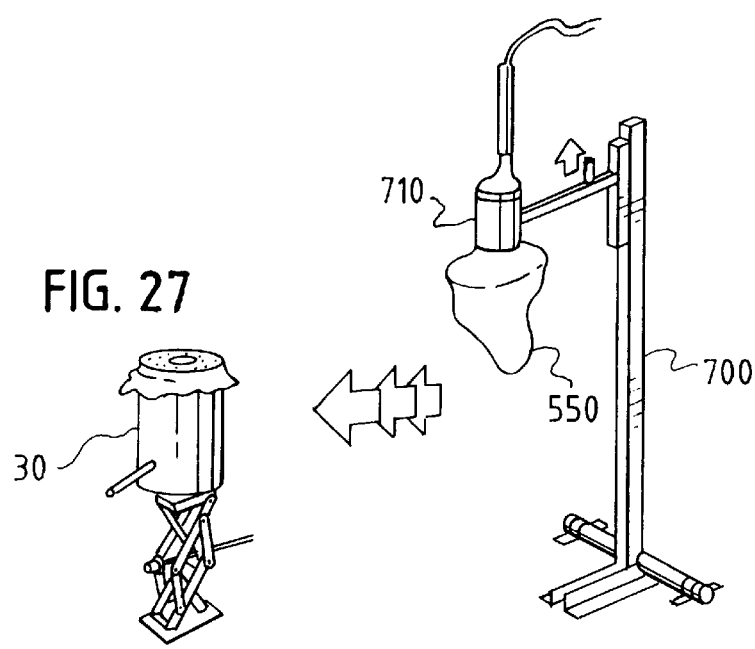
FIG. 27 illustrates a perspective view of the alignment vacuum forming jig of FIG. 20 after making the positive model of FIGS. 24–26 and the removal of the negative mold of FIG. 20 in an embodiment of a step in preparing an exoskeletal prosthesis following the steps of FIGS. 24–26 in a method of the present invention.

3. After the positive model is create as illustrated in FIGS. 24–26, disconnect the air hoses to the negative mold (dilatancy device), then lift the positive model and remove the dilatancy device away from the CIR AVF jig as is shown in FIG. 27.

Figure 28:
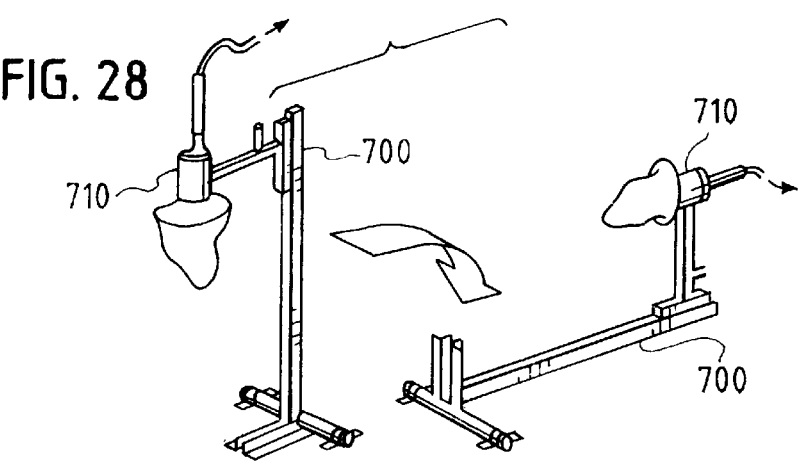
FIG. 28 illustrates a perspective view of the alignment vacuum forming jig having the positive model of FIG. 27 tilted from a vertical position to a horizontal position in an embodiment of a step in preparing an exoskeletal prosthesis following the step of FIG. 27 in a method of the present invention.

4. Tilt the CIR AVF jig 710 from a vertical position to a horizontal position and modify the positive model as needed as shown in FIG. 28.

Figure 29:
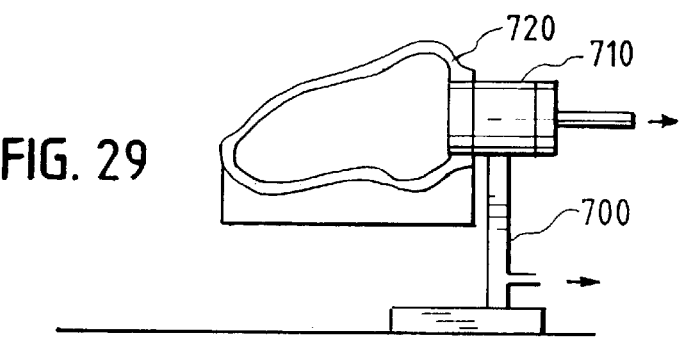
FIG. 29 illustrates a side elevation view of the horizontally tilted alignment vacuum forming jig having the positive model of FIG. 28 in an embodiment of a step of preparing a polypropylene socket by drape forming in preparing an exoskeletal prosthesis following the step of FIG. 28 in a method of the present invention.

6. Drape the softened polypropylene plastic 720 over the positive model (with or without pelite liner) with the seam line in the back as is illustrated in FIG. 29. Trim the excessive plastic while it is still hot and soft. Use a hot iron to smoothen the seam line so that the next layer of plastic can form over the seam line with a smooth finishing surface.

C. Determine the Position of Ankle Block

Figure 30:
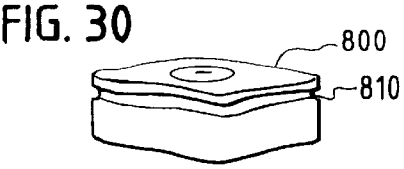
FIG. 30 illustrates a perspective view of one embodiment of an ankle block of the present invention.
Figure 31:
FIG. 31 illustrates a side elevation view of the ankle block of FIG. 30.

1. A specially designed ankle block 800 is used in the fabrication of the prosthetic shank using a dilatancy system as is shown in FIGS. 30–31. The ankle block is placed over the prosthetic foot, which is inserted in the shoe.

Figure 32:
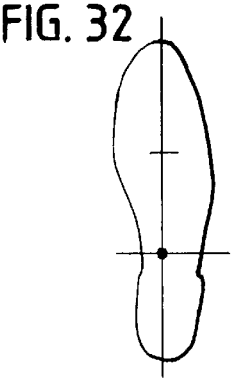
FIG. 32 illustrates a plan view of a shoe trace having an alignment reference center in preparing an exoskeletal prosthesis in a method of the present invention.

2. Make a shoe trace and identify the "Alignment Reference Center" by drawing the longitudinal axis on the shoe tracing. Then divide the longitudinal axis into three equal sections. The Alignment Reference Center would be the junction of the middle and posterior thirds as is shown in FIG. 32.

Figure 33:
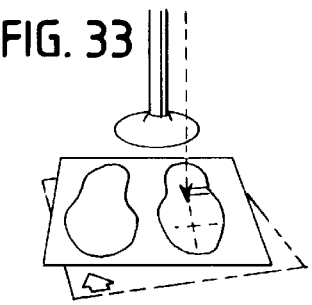
FIG. 33 illustrates a perspective view of the shoe tracing of FIG. 32 having the plumb line of FIG. 20 pointed at the alignment reference center in an embodiment of a step of preparing an exoskeletal prosthesis following the step of FIG. 29 in a method of the present invention.

3. Move the shoe tracing around until the plumb line is pointing at the alignment reference center. Adjust the degree of toe out by turning the shoe tracing around the alignment reference center, then tape the shoe tracing to the working table as is illustrated in FIG. 33.

Figure 34:
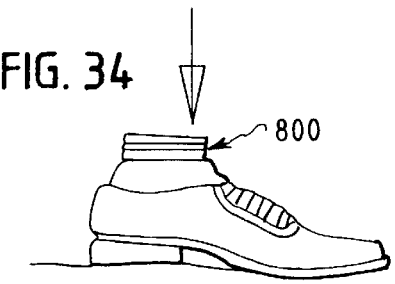
FIG. 34 illustrates a side elevation view of a prosthetic foot including the ankle block of FIG. 30 placed in the aligned shoe tracing of FIG. 33 in an embodiment of a step of preparing an exoskeletal prosthesis following the step of FIG. 33 in a method of the present invention.

4. Bring the foot-shoe unit with the ankle block on top of the prosthetic foot to match the shoe tracing as is shown in FIG. 34.

5. Lower down the plumb line and locate the alignment reference center on the ankle block. Then determine the height of the ankle block from the surface of the working table as can be seen in FIG. 34, thus determining the distance between the socket and the ankle block.

Figure 35:
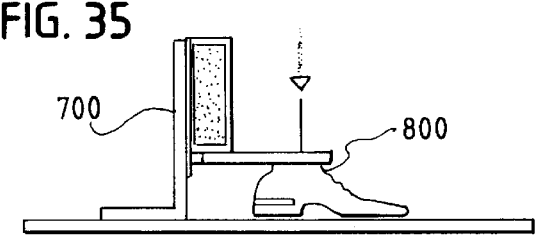
FIG. 35 illustrates a fragmentary, side elevation view of the prosthetic foot including the ankle block of FIG. 34 including a position attachment on the alignment vacuum forming jig of FIG. 20 in an embodiment of a step of preparing an exoskeletal prosthesis following the step of FIG. 34 in a method of the present invention.

6. Transfer the ankle block 800 to the position attachment of the CIR AVF jig 700 as is shown in FIG. 35.

7. Attach a latex glove 805, or any other type of latex cylinder or balloon, without digits to the groove 810 on the ankle block 800 leaving the thumb point up. Tape the other end of the glove to the prosthetic socket and seal the space in the glove except for the thumb, which had its tip cut open as shown in FIGS. 36a–e. As will be appreciated, any latex balloon or device having at least three openings may be used.

D. Preparing Positive Model of the Shank

1. Fill the glove with sand from a funnel 815 or other type of plastic container, through the opened thumb of the glove as is illustrated in FIG. 37, then seal the thumb and mold the sand mass into a proper shape of a limb shank 900.

2. Connect the vacuum tube to the base of ankle block 800 and remove air from inside the sand in the glove to form a solid mass for vacuum forming the polypropylene shank 920 as is shown in FIG. 38.

E. Joining the Socket-Shank to the Foot-Shoe Unit.

Figure 39:
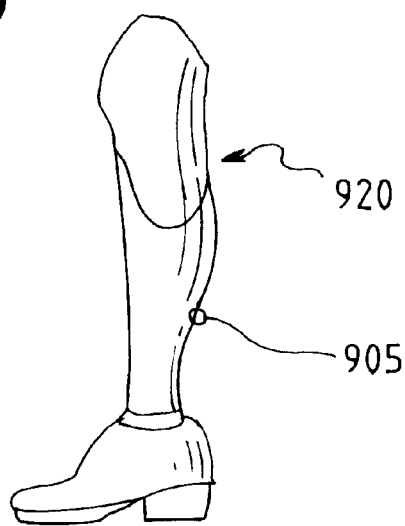
FIG. 39 illustrates a side elevation view of the polypropylene shank of FIG. 38 including the prosthetic foot of FIG. 34 in an embodiment of a step of preparing an exoskeletal prosthesis following the step of FIG. 38 in a method of the present invention.
Figure 40:
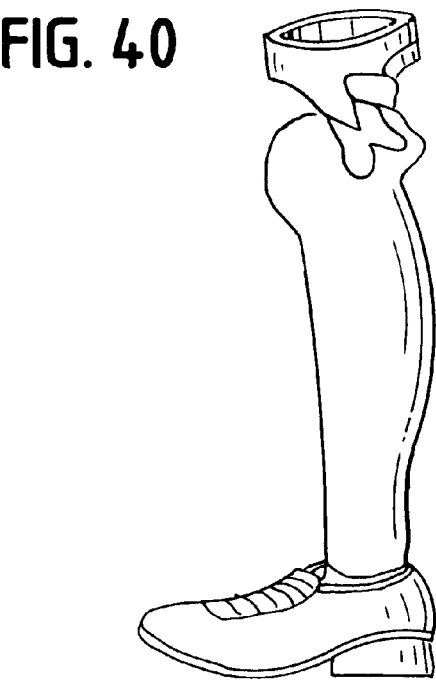
FIG. 40 illustrates an exoskeletal prosthesis including a supracondylar suspension strap in an embodiment of a step of preparing an exoskeletal prosthesis following the step of FIG. 39 in a method of the present invention.
Figure 41:
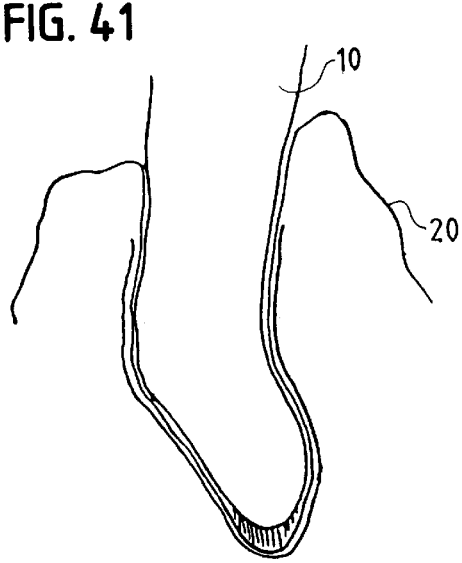
FIGS. 41–51 illustrate side elevation, sectional views of a residual limb, a negative mold, and a positive model in embodiments of the steps of preparing a positive model in an alternative method of the present invention.

1. Once the drape forming of the shank is done, open a one-inch hole 905 in the back of the shank to drain the sand and remove the latex glove out of the positive model as is shown in FIG. 39. Finally, attach the foot-shoe unit to the ankle block, which is now embedded inside the shank. Once the supracondylar suspension strap is attached, the prosthesis is ready for use as described in FIG. 40.

It should be understood that various changes and modifications preferred in the embodiment described herein will be apparent to those skilled in the art. Such changes and modifications can be made without departing from the spirit and scope of the present invention and without demising the attendant advantages. It is therefore intended that such changes and modifications be covered by the appended claims.

What is claimed is:

1. A device for making a socket for a prosthesis, the device comprising:
   a container filled with sand adapted to hold a residual limb such that the sand covers at least a portion of the residual limb;
   a vacuum source attached to the container adapted to remove air from the container forming a negative mold of the residual limb upon removal of the limb from the container;
   a mandrel positioned within the negative mold, the negative mold adapted to be filled with sand about the mandrel; and
   a pliable sheet adapted to cover the residual limb and further adapted to form a seal on the container such that a vacuum may be drawn on the mandrel by a second vacuum source wherein a positive model is formed after detachment of the vacuum source from the container and removal of the mandrel.

2. The device of claim 1 further comprising a jack, the jack aligning the container to the limb.

3. The device of claim 1 further comprising a plastic bag, the plastic bag covering the limb for ease of removal from the negative mold.

4. The device of claim 1 further comprising padding, the padding positioned over prominent areas of the limb wherein pressure relief is needed.

5. The device of claim 1 further comprising a wedge, the wedge added to a supracondylar area to avoid undercut during removal of the limb.

6. The device of claim 1 further comprising a sock, the sock secured over the limb, but underneath the bag for creating a smooth inner surface of the negative mold.

7. The device of claim 1 further comprising a sponge, the sponge positioned about the limb for an improved posterior trim line.

8. The device of claim 1 wherein the pliable sheet is a latex sleeve, the sleeve covering the limb upon insertion into the container such that the sleeve can be rolled to seal the container while remaining on the limb.

9. The device of claim 1 further comprising:
   a former, the former having an upper layer and a base wherein the positive model is positioned between the upper layer and the base, the upper layer comprising a healed material such that the material is draped over the positive model as the upper layer contacts the base; and
   a third vacuum source connected to the base of the former such that as the upper layer contacts the base, a vacuum may be drawn on the space between the heated material and the positive model by the third vacuum source forming a prosthetic socket.

10. The device of claim 1 further comprising:
    an ankle block having a groove and a central cavity;
    a pliable bag having at least three openings, the bag secured to the groove of the ankle block at a first opening, attached at a second opening to the positive model and fastened to a removable tube for inserting sand into the glove at a third opening;

a third vacuum source attached to the ankle block over the central cavity with a pliable cuff such that a vacuum may be drawn on the bag to form a solid shank;

a former, the former having an upper layer and a base wherein the shank is positioned between the upper layer and the base, the upper layer comprising a heated material such that the material is draped over the shank as the upper layer is brought into contact with the base; and a fourth vacuum source connected to the base of the former such that as the upper layer contacts the base, a vacuum may be drawn on the space between the heated material and the shank.

11. A device for making a socket for a prosthesis, the device comprising:

a latex bag for covering a residual limb;

a container filled with sand adapted to hold the residual limb such that the sand covers at least a portion of the stump;

a vacuum source attached to the container adapted to remove air from the container forming a negative mold of the residual limb;

a connector, the connector comprising a pipe having a top opening and a bottom opening, the pipe further having an air outlet attached to the side of the pipe, the bottom opening of the pipe sealed to the container with a latex cuff;

a casting balloon, the balloon inserted through the top opening of the pipe into the negative mold and secured to the top opening of the pipe such that a vacuum may be drawn on an area between the negative mold and the casting balloon by a second vacuum source attached to the air outlet of the pipe;

a mandrel positioned within the casting balloon, the casting balloon adapted to be filled with sand about the mandrel;

a latex covering, the latex covering forming a seal between the casting balloon and the mandrel such that a vacuum may be drawn on the mandrel by a third vacuum source wherein the air can be removed from the casting balloon and a positive model of the residual limb is formed after detachment of the first and second vacuum sources and removal of die casting balloon.

12. The device of claim 11 further comprising a jack, the jack aligning the container to the limb.

13. The device of claim 11 further comprising a plastic bag, the plastic bag covering the limb for ease of removal from the negative mold.

14. The device of claim 11 further comprising padding, the padding positioned over prominent areas of the limb wherein pressure relief is needed.

15. The device of claim 11 further comprising a wedge, the wedge added to a supracondylar area to avoid undercut during removal of the limb.

16. The device of claim 11 further comprising a sock, the sock secured over the limb for creating a smooth inner surface of the negative mold.

17. The device of claim 11 further comprising a sponge, the sponge positioned about the limb for an improved posterior trim line.

18. The device of claim 11 further comprising:

a former, the former having an upper layer and a base wherein the positive model is positioned between the upper layer and the base, the upper layer comprising a heated material such that the material is draped over the positive model as the upper layer contacts the base; and a fourth air vacuum source connected to the base of the former such that as the upper layer contacts the base, a vacuum may be drawn on the space between the heated material and the positive model by the fourth vacuum source forming a prosthetic socket.

19. The device of claim 11 further comprising:

an ankle block having a groove and a central cavity;

a pliable bag having at least three openings, the bag secured to the groove of the ankle block at a first opening, attached at a second opening to the positive model and secured to a removable tube for inserting sand into the bag at a third opening;

a fifth vacuum source attached to the ankle block over the central cavity with a pliable cuff such that a vacuum may be drawn on the bag to form a solid shank;

a former, the former having an upper layer and a base wherein the shank is positioned between the upper layer and the base, the upper layer comprising a heated material such that the material is draped over the shank as the upper layer is brought into contact with the base; and a sixth vacuum source connected to the base of the former such that as the upper layer contacts the base, a vacuum may be drawn on the space between the heated material and the shank.

20. A method for making a socket for a prosthesis comprising the steps of:

placing a residual limb having a pliable cover into a container;

adding sand to the container around the covered limb;

stretching the pliable cover around the container such that the container is sealed;

removing the air from within the container such that the sand becomes a solid around the limb;

withdrawing the limb from the container to form a negative mold of the residual limb;

inserting a mandrel into the negative mold;

adding sand to the negative mold around the mandrel;

stretching the pliable cover such that the container is sealed around the mandrel;

removing the air from within the negative mold;

adding air to the container such that the negative mold becomes fluidized and a positive model is formed about the mandrel for removal from the container.

* * * * *